(12) United States Patent
Itoh

(10) Patent No.: US 8,697,378 B2
(45) Date of Patent: Apr. 15, 2014

(54) METHOD AND KIT FOR QUANTITATIVE DETERMINATION FOR SMALL, DENSE PARTICLE LOW DENSITY LIPOPROTEINS

(75) Inventor: Yasuki Itoh, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 620 days.

(21) Appl. No.: 12/065,125

(22) PCT Filed: Aug. 31, 2006

(86) PCT No.: PCT/JP2006/317243
§ 371 (c)(1),
(2), (4) Date: Feb. 28, 2008

(87) PCT Pub. No.: WO2007/026829
PCT Pub. Date: Mar. 8, 2007

(65) Prior Publication Data
US 2009/0263844 A1 Oct. 22, 2009

(30) Foreign Application Priority Data
Aug. 31, 2005 (JP) ................................. 2005-252091

(51) Int. Cl.
*C12Q 1/60* (2006.01)
(52) U.S. Cl.
USPC .......................................................... 435/11
(58) Field of Classification Search
USPC .......................................................... 435/11
See application file for complete search history.

(56) References Cited

U.S. PATENT DOCUMENTS

| | | | |
|---|---|---|---|
| 4,440,662 A | 4/1984 | Tsuzuki et al. | |
| 5,858,279 A | 1/1999 | Lunski et al. | |
| 6,794,157 B1 | 9/2004 | Sugiuchi | |
| 2006/0154374 A1 | 7/2006 | Ito et al. | |

FOREIGN PATENT DOCUMENTS

| | | |
|---|---|---|
| EP | 0 095 580 A2 | 12/1983 |
| EP | 1 114 870 A1 | 7/2001 |
| EP | 1 132 482 A2 | 9/2001 |
| EP | 1 266 652 A1 | 12/2002 |
| JP | 2000-325097 | 11/2000 |
| WO | WO 00/17388 | 9/1998 |
| WO | WO 2004/053500 A1 | 6/2004 |

OTHER PUBLICATIONS

Fei et al. "Evaluation of two different homogeneous assays for LDL-cholesterol in lipoprotein-X-positive", Clinical Chemistry, 2000, 46(9):1351-1356.*
Williams et al. "Mechanisms by which lipoprotein lipase alters cellular metabolism of lipoprotein, low density lipoprotein, and nascent lijpoproteins", JBC, 1992, 267(19):13284-13292.*
Supplementary European Search Report EP 06 79 7203.
Hiroyuki Sugiuchi et al., "omogeneous assay for measuring low-density lipoprotein cholesterol in serum with triblock copolymer and α-cyclodextrin sulfate", Clinical Chemistry 44:3, 522-531 (1998).
European Office Action EP 06797203.4 dated Nov. 3, 2009.

* cited by examiner

*Primary Examiner* — Bin Shen
(74) *Attorney, Agent, or Firm* — Foley & Lardner LLP

(57) ABSTRACT

A rapid and convenient method capable of performing fractional measurement of small, dense LDLs without pretreatment of a specimen, which is adaptable for an autoanalyzer, is provided. A method for quantitatively determining small, dense LDL cholesterol is provided, which comprises adding enzymes for cholesterol measurement to a test sample in the presence of a polyoxyethylene-polyoxypropylene copolymer or a derivative thereof, causing the polyoxyethylene-polyoxypropylene copolymer or the derivative thereof to selectively act on small, dense LDLs among lipoproteins, and then measuring the amount of cholesterol generated.

5 Claims, 1 Drawing Sheet

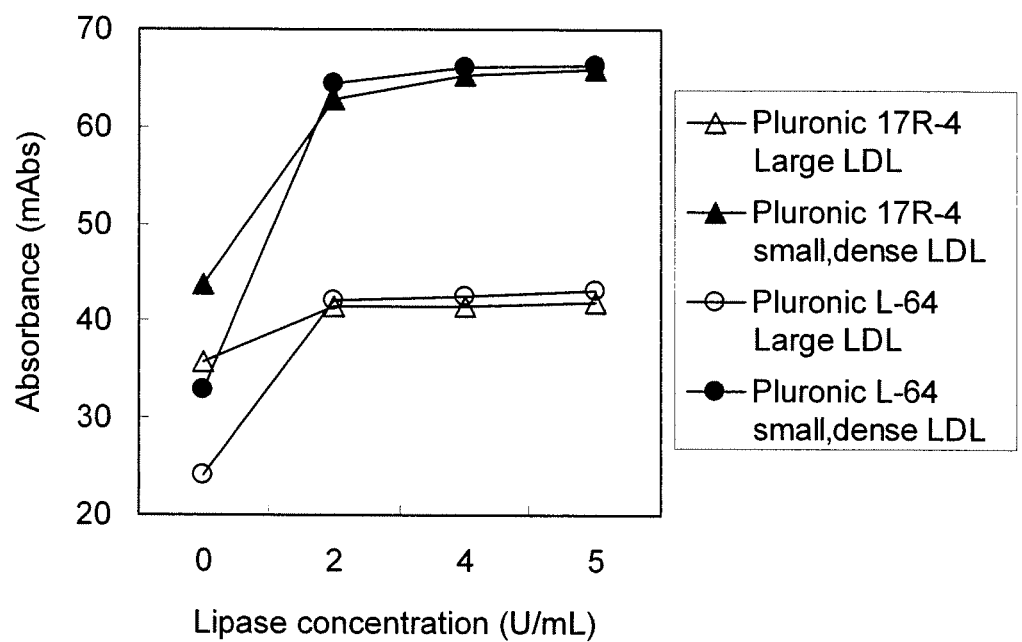

METHOD AND KIT FOR QUANTITATIVE DETERMINATION FOR SMALL, DENSE PARTICLE LOW DENSITY LIPOPROTEINS

TECHNICAL FIELD

The present invention relates to a method and a reagent for measurement of cholesterol in small, dense lipoproteins (LDLs), which is important for diagnosis of arteriosclerosis.

BACKGROUND ART

Low density lipoproteins (LDLs) play a major role in cholesterol transport in the blood and are risk factors for arteriosclerosis. It is known that small, dense lipoproteins, which are particularly small in particle size among LDLs and higher in specific gravity compared with standard LDLs, have arteriosclerosis-inducing ability at a level several-fold higher than that of normal LDLs. Increase of small, dense LDLs is one of the major risk factors for arteriosclerosis. It is clinically very important to perform a fractional measurement for such small, dense LDLs.

Examples of conventional methods for measurement of small, dense LDLs include an ultracentrifugation method, an electrophoresis method, and a method using high performance liquid chromatography. These methods are not convenient since they require expensive facilities and much time for measurement.

An example of a method for measuring small, dense LDLs using an autoanalyzer is a method (JP Patent Publication (Kokai) No. 2003-28882 A) that involves suspending or dissolving small particle LDLs with the use of differences in ionic strength and then conducting measurement on the small particle LDLs with the use of differences in absorbance. However, differences in absorbance are measured based on turbidity according to such method, and thus specificity and accuracy have been insufficient.

Furthermore, a method (WO2004/053500) that involves measuring cholesterol or triglycerides in small, dense LDLs through the use of a combination of a separation agent comprising polyanions and a divalent cation and a reagent adaptable for an autoanalyzer is known. This method is capable of measuring lipid components in small, dense LDLs more conveniently than an ultracentrifugation method or an electrophoresis method. Furthermore, the method is excellent in specificity and accuracy. However, the method requires pretreatment of specimens and a procedure for separating LDLs into small, dense LDLs and LDLs other than such LDLs.

DISCLOSURE OF THE INVENTION

Object to be Achieved by the Invention

An object of the present invention is to provide a rapid and convenient method for fractional measurement conducted on small, dense LDLs without pretreatment of a specimen, which is adaptable for an autoanalyzer.

Means to Achieve the Object

The present inventors have studied selective measurement of cholesterol in small, dense LDLs by causing in advance a surfactant that has reactivity with such small dense LDLs, which is different from its reactivity with the other LDLs, to act, when cholesterol in a test sample containing various lipoproteins is measured using cholesterol esterase and any of cholesterol oxidase, or cholesterol dehydrogenase. As a result, the present inventors have discovered that a polyoxyethylene-polyoxypropylene copolymer or a derivative thereof selectively acts on the small dense LDL and that cholesterol in the small dense LDL can be measured. Thus, the present inventors have completed the present invention.

Specifically, the present invention provides the following methods and kits.

(1) A method for quantitatively determining small, dense LDL cholesterol, comprising adding enzymes for cholesterol measurement to a test sample in the presence of a polyoxyethylene-polyoxypropylene copolymer or a derivative thereof, causing the polyoxyethylene-polyoxypropylene copolymer or the derivative thereof to selectively act on small, dense LDLs among lipoproteins, and then measuring the amount of cholesterol generated.

(2) The method according to (1), comprising further adding a nonionic and/or anionic surfactant.

(3) The method according to (1) or (2), in which the enzymes for cholesterol measurement comprise cholesterol esterase as well as cholesterol oxidase or cholesterol dehydrogenase.

(4) The method according to any one of (1) to (3), comprising further adding phospholipase and/or lipoprotein lipase.

(5) The method according to any one of (1) to (4), comprising, before causing the polyoxyethylene-polyoxypropylene copolymer or the derivative thereof to selectively act on small, dense LDLs among lipoproteins, leading cholesterol in lipoproteins other than the small, dense LDLs to the outside of the reaction system for quantitative determination of the small, dense LDL cholesterol.

(6) A kit for quantitative determination of small, dense LDL cholesterol comprising a polyoxyethylene-polyoxypropylene copolymer or a derivative thereof and enzymes for cholesterol measurement, which is used for measuring the amount of generated cholesterol by adding the enzymes for cholesterol measurement to a test sample in the presence of the polyoxyethylene-polyoxypropylene copolymer or the derivative thereof and then causing the polyoxyethylene-polyoxypropylene copolymer or the derivative thereof to selectively act on small, dense LDLs among lipoproteins.

(7) The kit for quantitative determination of small, dense LDL cholesterol according to (6), further comprising a nonionic and/or anionic surfactant.

(8) The kit for quantitative determination of small, dense LDL cholesterol according to (6) or (7), in which the enzymes for cholesterol measurement comprise cholesterol esterase as well as cholesterol oxidase or cholesterol dehydrogenase.

(9) The kit for quantitative determination of small, dense LDL cholesterol according to any one of (6) to (8), further comprising phospholipase and/or lipoprotein lipase.

(10) The kit for quantitative determination of small, dense LDL cholesterol according to any one of (6) to (9), comprising a reagent for leading, before causing the polyoxyethylene-polyoxypropylene copolymer or the derivative thereof to selectively act on small, dense LDLs among lipoproteins, cholesterol in the lipoproteins other than the small, dense LDLs to the outside of the reaction system for quantitative determination of the small, dense LDL cholesterol.

(11) A method for quantitative determination of small, dense LDL cholesterol in a test sample, comprising the steps of adding enzymes for cholesterol measurement to a test sample in the presence of a polyoxyethylene-polyoxypropylene copolymer or a derivative thereof, causing the polyoxyethylene-polyoxypropylene copolymer or the derivative thereof to selectively act on small, dense LDLs among lipoproteins, and measuring generated cholesterol.

(12) A reagent for quantitative determination of small, dense LDL cholesterol in a test sample containing small, dense LDL cholesterol, comprising a polyoxyethylene-polyoxypropylene copolymer or a derivative thereof.

(13) Use of a polyoxyethylene-polyoxypropylene copolymer as a reagent for quantitative determination of small, dense LDL cholesterol in a test sample containing small, dense LDL cholesterol.

Effect of the Invention

Small, dense LDLs among lipoproteins can be directly and selectively subjected to measurement by adding a polyoxyethylene-polyoxypropylene copolymer or a derivative thereof to a test sample containing the lipoproteins without performing any fractionation using filters or centrifugation.

This description hereby incorporates the entire content of the description and/or the drawings of Japanese Patent Application No. 2005-252091, which is the basis of the priority claim of this application.

BRIEF DESCRIPTION OF THE DRAWINGS

FIG. 1 shows reactivity to large LDLs and small, dense LDLs when lipoprotein lipase was added.

BEST MODE FOR CARRYING OUT THE INVENTION

The present invention will be explained in detail as follows.

A lipoprotein can be fractionated roughly into VLDLs, LDLs, and HDLs. LDLs are sub-fractionated into small, dense LDLs, and other sub-fractions. A small, dense LDL is also referred to as a small particle LDL, an SLDL (small LDL), or a dense LDL. LDLs other than a small particle LDL is sometimes referred to as LLDLs (large LDLs) or light LDLs. These fractions and sub-fractions may be distinguished based on particle size or specific gravity. The particle sizes (or particle diameters) of VLDLs range from 30 nm to 80 nm (30 nm to 75 nm), those of LDLs range from 22 nm to 28 nm (19 nm to 30 nm), and those of HDLs range from 7 nm to 10 nm, although such figures may vary depending on researcher. The specific gravity figures for VLDLs are 1.006 or less, those for LDLs range from 1.019 to 1.063, and those for HDLs range from 1.063 to 1.21. The diameters of LDL particles can be measured by gradient gel electrophoresis (GGE) (JAMA, 260, p. 1917-21, 1988) or NMR (HANDBOOK OF LIPOPROTEIN TESTING 2nd Edition, Edited by Nader Rifai et al. p. 609-623, AACC PRESS: The Fats of Life Summer 2002, LVDD 15 YEAR ANNIVERSARY ISSUE, Volume AVI No. 3, p. 15-16). Specific gravity can be determined based on analyses by ultracentrifugation (Atherosclerosis, 106, p. 241-253, 1994: Atherosclerosis, 83, p. 59, 1990).

The small, dense LDLs to be measured by the method of the present invention are, in general, sub-fractions of LDL fractions, with diameters that range from approximately 22.0 nm to approximately 25.5 nm and figures for specific gravity that range from 1.040 to 1.063. The reason why LDLs are sub-fractionated based on particle size is that small LDLs among LDLs need to be fractionally measured because such LDLs with small particle diameters have a high tendency of inducing arteriosclerosis and are higher in malignancy than other LDLs. The distributions of diameter and specific gravity of LDLs are continuous. Thus, it is impossible to clearly determine that an LDL with a specific gravity that is at the aforementioned level or higher shows a particularly high degree of malignancy. Thus specific gravity values ranging from 1.040 to 1.063 described above do not constitute an established characteristic of small, dense LDLs, but rather are values obtained by division based on the median point regarding the specific gravity range between 1.019 and 1.063, which is widely used and has been established as the specific gravity of LDLs. For example, in another report, small, dense LDLs are fractionated in the range between 1.044 and 1.060 (Atherosclerosis: 106 241-253 1994). There are some differences among researchers on how to set the range of specific gravity for small, dense LDLs. In all cases, the presence of small, dense LDLs are associated with clinical malignancy when fractionation is performed using such specific gravity ranges.

In the present invention, small, dense LDLs are defined as an LDL that has a low specific gravity among LDLs and that has a higher tendency of inducing arteriosclerosis, clinically, than other LDLs. Preferably, small, dense LDLs have a specific gravity within a range higher than the median point for the entire specific gravity range for LDLs. More preferably, a small, dense LDL is an LDL with a specific gravity within the specific gravity range between 1.040 and 1.063.

The method of the present invention is generally performed within an autoanalyzer. The method of the present invention is performed in the presence of a surfactant that causes enzymes for cholesterol measurement (e.g., cholesterol esterase, cholesterol oxidase, or cholesterol dehydrogenase) to act selectively on small, dense LDLs for the purpose of measuring small, dense LDL cholesterol via separation and differentiation of small, dense LDL cholesterol from large LDL cholesterol. Moreover, the method can also be performed in the presence of a surfactant that suppresses enzymes for cholesterol measurement from acting on lipoproteins other than small, dense LDLs. From a different perspective, a step of causing enzymes for cholesterol measurement to selectively act on small, dense LDLs can be said to be a step of suppressing enzymes for cholesterol measurement from acting on lipoproteins other than the small, dense LDLs. As a result, the two steps are the same and surfactants capable of achieving both purposes can indicate the same surfactant. The above surfactant can be used with a surfactant that enhances the activity of enzymes for cholesterol measurement, such as cholesterol esterase, cholesterol oxidase, or cholesterol dehydrogenase, or it may be used independently.

An example of a surfactant as described above that causes enzymes for cholesterol measurement to selectively act on small, dense LDLs is a polyoxyethylene-polyoxypropylene copolymer or a derivative thereof. The polyoxyethylene-polyoxypropylene copolymer or the derivative thereof selectively acts on small, dense LDLs, resulting in suppression of the action of cholesterol esterase as well as cholesterol oxidase or cholesterol dehydrogenase on lipoproteins other than small, dense LDLs. When the polyoxyethylene-polyoxypropylene copolymer or a derivative thereof are caused to selectively act on small, dense LDLs in a test sample, cholesterol in the small, dense LDLs is selectively liberated and then enzymes for cholesterol measurement are caused to react with cholesterol in small, dense LDLs. The phrase "causing a polyoxyethylene-polyoxypropylene copolymer or a derivative thereof to selectively act on small, dense LDLs among lipoproteins" means that cholesterol in the small, dense LDLs among lipoproteins is selectively liberated by the action of the polyoxyethylene-polyoxypropylene copolymer or the derivative thereof. The phrase "causing . . . to selectively act on small, dense LDLs" means to cause the polyoxyethylene-polyoxypropylene copolymer or the derivative thereof to mainly act on the small, dense LDLs among lipoproteins and it preferably means to cause the same to act only on the small, dense LDL. Cholesterol can be measured by causing enzymes for cholesterol measurement to react with the thus liberated cholesterol.

An example of the polyoxyethylene-polyoxypropylene copolymer or the derivative thereof is a compound represented by general formulae (I), (II), and (III):

RO—(C$_2$H$_4$O)$_a$—(C$_3$H$_6$O)$_b$—(C$_2$H$_4$O)$_c$—H  (I);

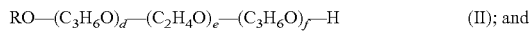

RO—(C$_3$H$_6$O)$_d$—(C$_2$H$_4$O)$_e$—(C$_3$H$_6$O)$_f$—H  (II); and

[wherein a, b, and c, and d, e, and f denote integers and R denotes a hydrogen atom or linear or branched alkyl]

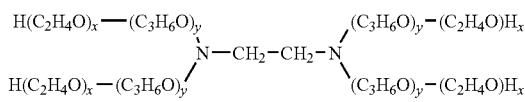

[wherein x and y denote integers]

In (I), the number of polyoxypropylene ("b" in the formula) preferably ranges from 1 to 200, more preferably ranges from 20 to 150, and particularly preferably ranges from 30 to 100. The number of each polyoxyethylene ("a" and "c" in the formula) preferably ranges from 1 to 200, more preferably ranges from 1 to 100, and particularly preferably ranges from 1 to 60. A linear or branched alkyl group represented by R has a carbon number preferably ranging from C1 to C30 and particularly preferably ranging from C2 to C25. In (II), the number of polyoxypropylene ("e" in the formula) preferably ranges from 20 to 100 and the number of each polyoxyethylene ("d" and "f" in the formula) preferably ranges from 1 to 60. In (III), the number of polyoxypropylene ("y" in the formula) preferably ranges from 2 to 30. The number of polyoxyethylene ("x" in the formula) preferably ranges from 1 to 50 and particularly preferably ranges from 1 to 30.

The concentration of the polyoxyethylene-polyoxypropylene copolymer or the derivative thereof preferably ranges from 0.1 g/L to 10 g/L, more preferably ranges from 0.3 g/L to 5 g/L, and particularly preferably ranges from 0.5 g/L to 3 g/L. Alternatively, the concentration of the same preferably ranges from 0.01% (w/w) to 1% (w/w), more preferably ranges from 0.03% (w/w) to 0.5% (w/w), and particularly preferably ranges from 0.05% (w/w) to 0.3% (w/w).

The specific gravity of a lipoprotein on which the polyoxyethylene-polyoxypropylene copolymer or the derivative thereof acts can be varied by varying the molecular weight of the hydrophobic group and the amount of ethylene oxide added. For example, the polyoxyethylene-polyoxypropylene copolymer or the derivative thereof, in which the hydrophobic group has a molecular weight ranging from 950 to 3850 and total ethylene oxide % ranges from 10% to 80%, can adequately act on small, dense LDLs.

When the polyoxyethylene-polyoxypropylene copolymer or the derivative thereof acts on LDLs other than small, dense LDLs, the LDLs on which the polyoxyethylene-polyoxypropylene copolymer or the derivative thereof acts are leaded in advance to the outside the reaction system for quantitative determination of the small, dense LDL cholesterol.

Examples of the polyoxyethylene-polyoxypropylene copolymer or the derivative thereof include pluronic (trademark)-based surfactants (e.g., BASF and ADEKA Corporation) such as pluronic 17R-4, pluronic L-64, pluronic PE3100, pluronic P-85, pluronic F-88, pluronic P-103, and pluronic F-127.

Furthermore, a nonionic surfactant and an anionic surfactant can be added to the above surfactant. These surfactants enhance the activity of cholesterol esterase as well as cholesterol oxidase or cholesterol dehydrogenase.

The hydrophilic lipophilic balance (HLB) of the above nonionic surfactants and anionic surfactants preferably ranges from 12 to 14.

Examples of such nonionic surfactants include polyoxyethylene derivatives. Particularly preferable examples of the same include polyoxyethylene alkylether, polyoxyethylene alkylenealkylether, and polyoxyethylene alkylphenylether. An alkyl group having a carbon number of 8 or more is preferred. For example, an octyl group and a nonyl group are preferred. Specific examples thereof include: polyoxyethylene alkylethers such as emulgen (trademark) 909, emulgen 100 series, emulgen 210P, 220, 306P, 320P, 404, 408, 409P, 420, 430, 705, 707, 709, 1108, 1118S-70, 1135S-70, 1150S-70, 4085, 2020G-HA, 2025G, and PI-20T (Kao Corporation), and PERSOFT NK60 (NOF Corporation); polyoxyethylenealkylenealkylethers such as emulgen LS-106, LS-110, LS-114, and MS-110 (Kao Corporation); polyoxyethyleneoctylphenylethers such as nonion HS-208, HS-210, NS-208.5, and NS210 (NOF Corporation); and other polyoxyethylene derivatives such as nonion L-4 and O-6 (NOF Corporation). Of these, emulgen 909, 109P, 409P, 709P, PI-20T, LS110 (Kao Corporation), PERSOFTNK60, nonion HS-208, HS-210, L-4, NS-208.5, NS-210, and O-6 (NOF Corporation) are preferred.

The concentration of such polyoxyethylene derivative preferably ranges from 0.1 g/L to 50 g/L and particularly preferably ranges from 0.5 g/L to 10 g/L. Alternatively, the concentration preferably ranges from 0.01% (w/w) to 5% (w/w) and particularly preferably ranges from 0.05% (w/w) to 1% (w/w).

As an anionic surfactant, sodium alkyl sulfate, sodium polyoxyethylene alkylether sulfate, or sodium alkylbenzenesulfonate is preferred. Specifically, Trux H-45 (NOF Corporation) and Succineed 3LN (NOF Corporation) that is disodium polyoxyethylene lauryl sulfosuccinate are preferred.

The concentration of such anionic surfactant preferably ranges from 0.1 g/L to 20 g/L and particularly preferably ranges from 0.5 g/L to 10 g/L. Alternatively, the concentration of the same preferably ranges from 0.01% (w/w) to 2% (w/w) and particularly preferably ranges from 0.05% (w/w) to 1% (w/w).

According to the present invention, small, dense LDL cholesterol is measured in an aqueous solution and preferably in a buffer solution. As a buffering agent to be used for a buffer solution is preferably a buffer solution containing amine, such as tris, triethanol amine, and Good's buffer solution. In particular, as Good's buffer solution, Bis-Tris, PIPES, BES, MOPSO, HEPES and POPSO are preferred. The pH of such buffer solution preferably ranges from 5 to 9. The concentration of such buffer solution preferably ranges from 10 mmol/L to 500 mmol/L.

When such surfactant is caused to act on lipoproteins, cholesterol in the lipoprotein is liberated. Enzymes (cholesterol esterase as well as cholesterol oxidase or cholesterol dehydrogenase) are caused to react with the cholesterol so that the cholesterol is degraded and oxidized.

Cholesterol esterase to be used in the present invention is not particularly limited, as long as it is an enzyme that hydrolyzes cholesterol ester. Animal- or microorganism-derived cholesterol esterase can be used. The concentration of cholesterol esterase preferably ranges from 0.01 U/mL to 50 U/mL and particularly preferably ranges from 0.1 U/mL to 10 U/mL.

Cholesterol oxidase to be used herein is not particularly limited, as long as it is an enzyme that is capable of oxidizing cholesterol. Animal- or microorganism-derived cholesterol oxidase can be used. The concentration of cholesterol oxidase preferably ranges from 0.01 U/mL to 20 U/mL and particularly preferably ranges from 0.1 U/mL to 1 U/mL.

Cholesterol dehydrogenase to be used herein is not particularly limited, as long as it is an enzyme capable of oxidizing cholesterol so as to reduce the oxidized coenzyme. Animal- or microorganism-derived cholesterol dehydrogenase can be used. The concentration of cholesterol dehydrogenase preferably ranges from 0.01 U/mL to 200 U/mL and particularly preferably ranges from 0.1 U/mL to 100 U/mL.

In the present invention, phospholipase and/or lipoprotein lipase can further be used to enhance reaction selectivity for small, dense LDLs.

As phospholipase, phospholipase A2, phospholipase C, phospholipase D, lysophospholipase, or the like can be used. The concentration employed herein preferably ranges from 0.01 U/mL to 10 U/mL, further preferably ranges from 0.01 U/mL to 5 U/mL, and particularly preferably ranges from 0.01 U/mL to 1 U/mL.

Lipoprotein lipase to be used herein is not particularly limited, as long as it is an enzyme capable of degrading lipoproteins. Animal- or microorganism-derived lipoprotein lipase can be used. The concentration of such lipoprotein lipase, which is employed herein, preferably ranges from 0.01 U/mL to 10 U/mL, further preferably ranges from 0.01 U/mL to 5 U/mL, and particularly preferably ranges from 0.01 U/mL to 1 U/mL.

When cholesterol esterase and cholesterol oxidase are used as enzymes for cholesterol measurement, hydrogen peroxide is generated by the enzyme reaction. The thus generated hydrogen peroxide can be quantitatively determined through measurement at a wavelength between 400 nm and 700 nm using a dye (colored quinone) that is formed by the coupling reaction of a hydrogen donor and a hydrogen receptor in the presence of peroxidase.

As a hydrogen donor, an aniline derivative is preferred. Examples of such aniline derivative include N-ethyl-N-(2-hydroxy-3-sulfo propyl)-3-methylaniline (TOOS), N-ethyl-N-(2-hydroxy-3-sulfopropyl)-3,5-dimethylaniline (MAOS), N-ethyl-N-(3-sulfopropyl)-3-methylaniline (TOPS), N-(2-hydroxy-3-sulfopropyl)-3,5-dimethoxyaniline (HDAOS), N-(3-sulfopropyl)aniline (HALPS), and N-(3-sulfopropyl)-3-methoxy-5-aniline (HMMPS). The concentration of such hydrogen donor, which is employed herein, preferably ranges from 0.1 mmol/L to 1.5 mmol/L at a final concentration.

As a hydrogen receptor, 4-aminoantipyrine, methylbenzothiazolonhydrazone, or the like can be used.

When cholesterol esterase and cholesterol dehydrogenase are used as enzymes for cholesterol measurement, NAD(P)H is generated from NAD(P) by the enzyme reaction. The thus generated NAD(P)H can be quantitatively determined by measuring absorbance at 330 nm to 400 nm.

In the present invention, cholesterol contained in lipoproteins (e.g., HDLs or VLDLs, or Large LDLs) other than small, dense LDLs in a test sample may be leaded to the outside of the reaction system for quantitative determination of the small, dense LDL cholesterol, in order to further enhance the reaction selectivity for the small, dense LDLs. The phrase " . . . leaded to the outside of the reaction system for quantitative determination of small, dense LDL cholesterol" means: that cholesterol contained in HDLs, VLDLs, Large LDLs, or the like is eliminated or massed together so as to prevent the cholesterol from affecting quantitative determination of the small, dense LDL cholesterol; or that the cholesterol contained in HDLs, VLDLs, Large LDLs, or the like is inhibited so as to avoid the reaction thereof in the subsequent step.

The term "elimination" means to degrade a substance in a test sample so as to prevent the degraded product from being detected in the subsequent step. In this case, examples of a surfactant that acts on lipoproteins other than small, dense LDLs include polyoxyethylene derivatives with HDL values of 13 or more and 15 or less. Specific examples of the same include polyoxyethylene lauryl ether, polyoxyethylene cetyl ether, polyoxyethylene oleyl ether, polyoxyethylene higher alcohol ether, polyoxyethylene octylphenyl ether, polyoxyethylene nonylphenyl ether, and polyoxyethylene benzyl phenyl ether that are compounds with HLB values of 13 or more and 15 or less. The concentration of such surfactant preferably ranges from approximately 0.1 g/L to 10 g/L and more preferably approximately ranges from 0.3 g/L to 5.0 g/L. Alternatively the concentration of the same preferably ranges from approximately 0.01% (w/w) to 1% (w/w) and more preferably ranges from approximately 0.03% (w/w) to 0.5% (w/w).

In this case, examples of a method for eliminating cholesterol in lipoproteins other than small, dense LDLs includes a method that involves degrading hydrogen peroxide (generated by causing cholesterol esterase and cholesterol oxidase, in addition to the above surfactant, to act) into water and oxygen using catalase, and a method that involves causing a hydrogen donor to react with hydrogen peroxide using peroxidase, so as to perform conversion into colorless quinine. However, examples of such method to be employed herein are not limited thereto.

In the present invention, a monovalent cation and/or a divalent cation and a salt thereof can be used as an ionic strength adjuster. Addition of such ionic strength adjuster facilitates separation of small, dense LDLs. Specifically, sodium chloride, potassium chloride, magnesium chloride, manganese chloride, calcium chloride, lithium chloride, ammonium chloride, magnesium sulfate, potassium sulfate, lithium sulfate, ammonium sulfate, magnesium acetate, and the like can be used. The concentration employed herein ranges from 0 mmol/L to 100 mmol/L.

The reaction is preferably performed within a temperature range between 2° C. and 45° C. and further preferably between 25° C. and 40° C.

The reaction is preferably performed for 1 to 30 minutes and more preferably for 3 to 15 minutes.

Serum and plasma can be used as test samples in the present invention. However, examples of such a test sample are not limited thereto.

The term "aggregation" means that with the use of a coagulant for causing aggregation of substances in a test sample, an antibody against a substance in a test sample, or the like, so as to avoid detection of the aggregated product in the subsequent step. Here, such a coagulant induces aggregation by chemical reaction. Furthermore, such an antibody is an antibody against a specific lipoprotein fraction, so as to cause the immunoaggregation reaction. For example, a reaction solution can contain a lipoprotein coagulant if necessary. Examples of such lipoprotein coagulant include: polyanions or salts thereof such as phosphotungstic acid, heparin, and dextran sulfate; and divalent cations such as magnesium, manganese, and calcium.

Examples of an autoanalyzer to be used in the present invention include TBA-120FR•200FR (Toshiba), JCA-BM1250•1650•2250 (JEOL Ltd.), HITACHI7180•7700 (Hitachi), and AU2700 (OLYMPUS).

The method of the present invention comprises the $1^{st}$ step of adding a polyoxyethylene-polyoxypropylene copolymer or a derivative thereof, and enzymes for cholesterol measurement to a test sample, so as to liberate and degrade cholesterol in small, dense LDLs and the $2^{nd}$ step of quantitatively determining the degraded product of cholesterol. Since the polyoxyethylene-polyoxypropylene copolymer or the derivative thereof has high selectivity for the small, dense LDLs, the small, dense LDLs can be selectively quantitatively determined by the above steps. The method of the present invention may further comprises, before the $1^{st}$ step, the step of leading cholesterol that is contained in lipoproteins (e.g., HDLs or VLDLs, or Large LDLs) other than small, dense LDLs in a test sample to the outside of the reaction system for quantitative determination of small, dense LDL cholesterol. The step of leading such cholesterol to the outside of the reaction system for quantitative determination of small, dense LDL cholesterol refers to: a step of eliminating or causing aggregation of cholesterol that is contained in HDLs or VLDLs, Large LDLs, or the like, so as to prevent the cholesterol from affecting quantitative determination of small, dense LDL cholesterol; or a step of inhibiting such cholesterol so as to avoid reaction thereof in the subsequent step.

In the step of leading cholesterol that is contained in lipoproteins (e.g., HDLs or VLDLs, or Large LDLs) other than small, dense LDLs in a test sample to the outside of the reaction system for quantitative determination of small, dense LDL cholesterol, which is performed before the $1^{st}$ step, for example, enzymes for cholesterol measurement such as cholesterol esterase and cholesterol oxidase are added, the enzymes are caused to act on cholesterol contained in lipoproteins (e.g., HDLs or VLDLs, or Large LDLs) other than small, dense LDLs, and then the thus generated hydrogen peroxide is degraded by catalase, so that the cholesterol contained in the lipoproteins (e.g, HDLs or VLDLs, or Large LDLs) other than the small, dense LDLs can be leaded to the outside of the reaction system for quantitative determination of small, dense LDL cholesterol. Subsequently, a polyoxyethylene-polyoxypropylene copolymer or a derivative thereof may be added together with a surfactant to the system, if necessary. Hydrogen peroxide is generated from small, dense LDL cholesterol due to the action of enzymes for cholesterol measurement, the polyoxyethylene-polyoxypropylene copolymer or the derivative thereof, or furthermore a surfactant in the system. The hydrogen peroxide can then be quantitatively determined.

When the measurement method of the present invention is performed, reagents (to be used herein) may be divided into a plurality of reagent compositions. Examples of reagents to be used in the present invention include a polyoxyethylene-polyoxypropylene copolymer or a derivative thereof, enzymes for cholesterol measurement such as cholesterol esterase and cholesterol oxidase, a surfactant, catalase that degrades hydrogen peroxide, peroxidase for the formation of a dye from hydrogen peroxide via coupling reaction, a hydrogen donor, and a buffer solution. Division of these reagents into different reagent compositions is adequately performed in view of stability and the like of the reagents. For example, reagents are divided into two compositions: a $1^{st}$ reagent composition; and a $2^{nd}$ reagent composition. The $1^{st}$ reagent composition can comprise enzymes for cholesterol measurement such as cholesterol esterase and cholesterol oxidase and the $2^{nd}$ reagent composition can comprise a polyoxyethylene-polyoxypropylene copolymer or a derivative thereof, a surfactant for enhancement of the activity of such enzymes for cholesterol measurement, and the like. The $2^{nd}$ reagent composition may further comprise phospholipase or lipoprotein lipase. When such two reagent compositions are employed, the $1^{st}$ reagent composition is added to a test sample, followed by 1 to 10 minutes and preferably approximately 5 minutes of reaction. The $2^{nd}$ reagent composition is then added, followed by further 1 to 10 minutes and preferably approximately 5 minutes of reaction. The thus formed dye can be quantitatively determined.

The above $1^{st}$ step and $2^{nd}$ step of the present invention can also be performed using a test sample in which cholesterol contained in lipoproteins (e.g., HDLs or VLDLs, or Large LDLs) other than small, dense LDLs has been eliminated in advance. For example, a small, dense LDL fraction is separated by centrifugation from a specimen and then the fraction can be subjected to measurement.

The present invention also encompasses a reagent for measurement of small, dense LDL cholesterol, which comprises a polyoxyethylene-polyoxypropylene copolymer or a derivative thereof and is used for quantitative determination of small, dense LDL cholesterol in a test sample containing the small, dense LDL cholesterol.

The present invention further encompasses a kit for quantitative determination of small, dense LDL cholesterol. The kit comprises at least a polyoxyethylene-polyoxypropylene copolymer or a derivative thereof. The kit may further comprise enzymes for cholesterol measurement. The kit may further comprise a nonionic and/or anionic surfactant. The kit may further comprise a reagent for leading cholesterol in lipoproteins other than small, dense LDLs to the outside of the reaction system for quantitative determination of small, dense LDL cholesterol. The reagent for leading such cholesterol to the outside of the reaction system for quantitative determination of small, dense LDL cholesterol is a reagent for eliminating, causing aggregation of, and inhibiting the above cholesterol in lipoproteins other than the small, dense LDLs.

The present invention further encompasses the use of a polyoxyethylene-polyoxypropylene copolymer as a reagent for measurement of small, dense LDL cholesterol, which is used for quantitative determination of small, dense LDL cholesterol in a test sample containing the small, dense LDL cholesterol.

EXAMPLES

The present invention will be specifically explained based on the examples as follows. However, the present invention is not limited to the examples described below.

Example 1

The following reagent compositions were prepared such that various polyoxyethylene-polyoxypropylene copolymers were used in a second reagent composition.

| First reagent composition | |
|---|---|
| PIPES buffer solution, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% |
| TOOS | 2.0 mmol/L |

| Second reagent composition | |
|---|---|
| PIPES buffer solution, pH 7.0 | 50 mmol/L |
| Polyoxyethylene-polyoxypropylene copolymer | 0.3% |
| 4-aminoantipyrine | 4.0 mmol/L |

-continued

| Second reagent composition | |
|---|---|
| Peroxidase | 4.0 unit/mL |
| Sodium azide | 0.05% |

Thirty human serum samples were used as test samples.

300 μL of the 1$^{st}$ reagent composition was added to 4 μL of a serum sample, followed by 5 minutes of reaction at 37° C. 100 μL of the 2$^{nd}$ reagent composition was added and then reaction was performed for 5 minutes. Absorbance at 600 nm was measured.

A "SEIKEN" sd LDL-C reagent kit for measurement of small, dense LDL cholesterol (produced by DENKA SEIKEN Co., Ltd.) was used as a control for comparison, small, dense LDL cholesterol concentrations were compared by linear regression analysis. Table 1 shows the results. Table 1 is the list of correlation coefficients between the products of the present invention obtained via the use of various polyoxyethylene-polyoxypropylene copolymers and the "SEIKEN" sd LDL-C reagent kit for measurement of small, dense LDL cholesterol.

As shown in Table 1, measurement values obtained with the use of reagent compositions comprising various polyoxyethylene-polyoxypropylene copolymers showed good correlation with the measurement value obtained with the use of the "SEIKEN" sd LDL-C reagent kit for measurement of small, dense LDL cholesterol. This demonstrates that according to the method of the present invention, small, dense LDL cholesterol can be measured with good accuracy.

TABLE 1

| Polyoxyethylene-polyoxypropylene copolymer | Molecular weight of hydrophobic group | Total ethylene oxide % | Correlation coefficient |
|---|---|---|---|
| (1) Pluronic PE3100 | 950 | 10 | 0.787 |
| (2) Pluronic L-64 | 1750 | 40 | 0.710 |
| (3) Pluronic 17R-4 | 1700 | 40 | 0.792 |
| (4) Pluronic P-85 | 2250 | 50 | 0.630 |
| (5) Pluronic F-88 | 2250 | 80 | 0.695 |
| (6) Pluronic P-103 | 3250 | 30 | 0.758 |
| (7) Pluronic F-127 | 3850 | 70 | 0.708 |

Surfactant used in (1) was produced by BASF; and surfactants used in (2) to (7) were produced by ADEKA Corporation.

Example 2

The following reaction compositions were prepared such that the 2$^{nd}$ reagent composition of Example 1 was further supplemented with a nonionic surfactant.

| 1$^{st}$ reagent composition | |
|---|---|
| PIPES buffer solution, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% |
| TOOS | 2.0 mmol/L |

| 2$^{nd}$ reagent composition | |
|---|---|
| PIPES buffer solution, pH 7.0 | 50 mmol/L |
| Polyoxyethylene-polyoxypropylene copolymer | 0.3% |
| Polyoxyethylene nonylphenolether Emulgen 909 [produced by Kao Corporation] | 1% |
| 4-aminoantipyrine | 4.0 mmol/L |
| Peroxidase | 4.0 unit/mL |
| Sodium azide | 0.05% |

300 μL of the 1$^{st}$ reagent composition was added to 4 μL each of small, dense LDL fractions each with a cholesterol content of 100 mg/dL and large LDL fractions each with a cholesterol content of 100 mg/dL, which had been separated by an ultracentrifugation method, followed by 5 minutes of reaction at 37° C. 100 μL of the 2$^{nd}$ reagent composition was added and then the reaction was performed for 5 minutes. Absorbance at 600 nm was then measured.

As a result, whereas most of the small, dense LDL fractions reacted and were measured, only 67% of the large LDL fractions was measured. Specifically, through addition of the nonionic surfactant to the reagent composition, the reactivity of small, dense LDLs was more enhanced compared with the case where no such surfactant had been added.

Moreover, a similar experiment was performed using nonionic surfactants including 109P, 409P, 709P, PI-20T, and LS110 (Kao Corporation) and PERSOFTNK60, nonion HS-208, 210, L-4, NS-208.5, 210, and O-6 (NOF Corporation) instead of emulgen 909. Through addition of the nonionic surfactants to the reagent compositions, it could also be confirmed that the reactivity of small, dense LDLs was enhanced compared with the case in which no such surfactants had been added.

Therefore, cholesterol in small, dense LDLs can be efficiently measured through addition of such nonionic surfactant.

Example 3

Thirty human serum samples as test samples were subjected to measurement using the reagent compositions used in Example 2.

300 μL of the 1$^{st}$ reagent composition was added to 4 μL of a serum sample, followed by 5 minutes of reaction at 37° C. 100 μL of the 2$^{nd}$ reagent composition was added and then reaction was performed for 5 minutes. Absorbance at 600 nm was then measured.

Small, dense LDL cholesterol concentrations were compared by linear regression analysis using a "SEIKEN" sd LDL-C reagent kit (produced by DENKA SEIKEN Co., Ltd.) for measurement of small, dense LDL cholesterol as a control for comparison. Table 2 shows the results. Table 2 is the list of correlation coefficients between the products of the present invention obtained with the use of various polyoxyethylene-polyoxypropylene copolymers and nonionic surfactants and the "SEIKEN" sd LDL-C reagent kit for measurement of small, dense LDL cholesterol.

As shown in Table 2, measurement values obtained with the use of various polyoxyethylene-polyoxypropylene copolymers and nonionic surfactants showed good correlation with the measurement value obtained with the use of the "SEIKEN" sd LDL-C reagent kit for measurement of small, dense LDL cholesterol. Better correlation coefficients can be confirmed compared with those in Example 1. This demonstrates that small, dense LDL cholesterol can be measured with good accuracy by the method of the present invention that involves addition of a nonionic surfactant.

TABLE 2

| Polyoxyethylene-polyoxypropylene copolymer | Nonionic surfactant | Total ethylene oxide % | Correlation coefficient |
|---|---|---|---|
| (1) Pluronic PE3100 | Emulgen 909 | 10 | 0.819 |
| (2) Pluronic L-64 | Emulgen 909 | 40 | 0.756 |

Example 4

The following reaction compositions were prepared such that the $2^{nd}$ reagent composition of Example 1 was further supplemented with an anionic surfactant.

| $1^{st}$ reagent composition | |
|---|---|
| PIPES buffer solution, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% |
| TOOS | 2.0 mmol/L |

| $2^{nd}$ reagent composition | |
|---|---|
| PIPES buffer solution, pH 7.0 | 50 mmol/L |
| Polyoxyethylene-polyoxypropylene copolymer | 0.3% |
| Polyoxyethylene nonylphenolether | 1% |
| Trux H-45 [produced by NOF Corporation] | |
| 4-aminoantipyrine | 4.0 mmol/L |
| Peroxidase | 4.0 unit/mL |
| Sodium azide | 0.05% |

300 μL of the $1^{st}$ reagent composition was added to 4 μL each of small, dense LDL fractions each with a cholesterol content of 100 mg/dL and large LDL fractions each with a cholesterol content of 100 mg/dL, which had been separated by an ultracentrifugation method, followed by 5 minutes of reaction at 37° C. 100 μL of the $2^{nd}$ reagent composition was added and then the reaction was performed for 5 minutes. Absorbance at 600 nm was then measured.

As a result, whereas most of the small, dense LDL fractions reacted and were measured, only 69% of the large LDL fractions was measured. Specifically, through addition of the anionic surfactant to the reagent composition, the reactivity of small, dense LDLs was more enhanced compared with the case where no such surfactant had been added.

Moreover, a similar experiment was performed using Succineed 3LN (NOF Corporation) that is an anionic surfactant instead of Trux H-45. Through addition of the anionic surfactant to the reagent composition, it could also be confirmed that the reactivity of small, dense LDLs was more enhanced compared with the case where no such surfactant had been added.

Therefore, cholesterol in small, dense LDLs can be efficiently measured through addition of such anionic surfactant.

Example 5

Thirty human serum samples as test samples were subjected to measurement using the reagent compositions used in Example 4.

300 μL of the $1^{st}$ reagent composition was added to 4 μL of a serum sample, followed by 5 minutes of reaction at 37° C. 100 μL of the $2^{nd}$ reagent composition was added and then the reaction was performed for 5 minutes. Absorbance at 600 nm was then measured.

Small, dense LDL cholesterol concentrations were compared by linear regression analysis using a "SEIKEN" sd LDL-C reagent kit (produced by DENKA SEIKEN Co., Ltd.) for measurement of small, dense LDL cholesterol as a control for comparison. Table 3 shows the results. Table 3 is the list of correlation coefficients between the products of the present invention obtained with the use of various polyoxyethylene-polyoxypropylene copolymers and anionic surfactants and the "SEIKEN" sd LDL-C reagent kit for measurement of small, dense LDL cholesterol.

As shown in Table 3, measurement values obtained with the use of various polyoxyethylene-polyoxypropylene copolymers and anionic surfactants showed good correlation with the measurement value obtained with the use of the "SEIKEN" sd LDL-C reagent kit for measurement of small, dense LDL cholesterol. Better correlation coefficients can be confirmed compared with those in Example 1. This demonstrates that small, dense LDL cholesterol can be measured with good accuracy by the method of the present invention that involves addition of an anionic surfactant.

TABLE 3

| Polyoxyethylene-polyoxypropylene copolymer | Anionic surfactant | Total ethylene oxide % | Correlation coefficient |
|---|---|---|---|
| (1) Pluronic PE3100 | Succineed 3LN | 10 | 0.812 |
| (2) Pluronic L-64 | Trux H-45 | 40 | 0.744 |

Example 6

The following reagent compositions were prepared such that the $2^{nd}$ reagent composition of Example 1 was further supplemented with lipoprotein lipase having a concentration of 0, 2, 4, or 5 U/mL.

| $1^{st}$ reagent composition | |
|---|---|
| PIPES buffer solution, pH 7.0 | 50 mmol/L |
| Cholesterol esterase | 0.6 U/mL |
| Cholesterol oxidase | 0.5 U/mL |
| Catalase | 600 U/mL |
| Bovine serum albumin | 0.5% |
| TOOS | 2.0 mmol/L |

| $2^{nd}$ reagent composition | |
|---|---|
| PIPES buffer solution, pH 7.0 | 50 mmol/L |
| Polyoxyethylene-polyoxypropylene copolymer pluronic 17R-4 or pluronic L-64 [produced by ADEKA Corporation] | 0.3% |
| 4-aminoantipyrine | 4.0 mmol/L |
| Peroxidase | 4.0 unit/mL |
| Lipoprotein lipase LPL-311 [produced by TOYOBO Co., Ltd.] | 0, 2, 4, or 5 U/mL |
| Sodium azide | 0.05% |

300 μL of the 1$^{st}$ reagent composition was added to 4 μL each of small, dense LDL fractions each with a cholesterol content of 100 mg/dL and large LDL fractions each with a cholesterol content of 100 mg/dL, which had been separated by an ultracentrifugation method, followed by 5 minutes of reaction at 37° C. 100 μL of the 2$^{nd}$ reagent composition was added and then the reaction was performed for 5 minutes. Absorbance at 600 nm was then measured.

FIG. 2 shows the results.

As shown in FIG. 2, the reactivity of small, dense LDLs was significantly enhanced compared with the reactivity of large LDLs through addition of lipoprotein lipase to the reagent composition. Therefore, cholesterol in small, dense LDLs can be efficiently measured through addition of lipoprotein lipase.

All publications, patents, and patent applications cited in this description are herein incorporated by reference in their entirety.

The invention claimed is:

1. A method for quantitatively determining small, dense LDL cholesterol, comprising:

adding enzymes for cholesterol measurement to a test sample in the presence of a polyoxyethylene-polyoxypropylene copolymer represented by formula (II):

$$RO-(C_3H_6O)_d-(C_2H_4O)_e-(C_3H_6O)_f-H \quad (II),$$

wherein a is an integer between 1 and 200, b is an integer between 1 and 200, c is an integer between 1 and 200, d is an integer between 1 and 60, e is an integer between 20 and 100, and f is an integer between 1 and 60, wherein R denotes a hydrogen atom or linear or branched alkyl having a carbon number ranging from C1 to C30;

(ii) causing the polyoxyethylene-polyoxypropylene copolymer to selectively act on small, dense LDLs among lipoproteins, and then (iii) measuring the amount of cholesterol generated.

2. The method according to claim 1, comprising further adding a nonionic and/or anionic surfactant.

3. The method according to claim 1, wherein the enzymes for cholesterol measurement comprise cholesterol esterase as well as cholesterol oxidase or cholesterol dehydrogenase.

4. The method according to claim 1, further comprising adding phospholipase and/or lipoprotein lipase.

5. The method according to claim 1, further comprising, before step (ii), eliminating or aggregating cholesterols other than small, dense LDLs.

* * * * *